(12) United States Patent
Martin et al.

(10) Patent No.: US 8,448,532 B2
(45) Date of Patent: May 28, 2013

(54) ACTIVELY COOLED VAPOR PRECONCENTRATOR

(75) Inventors: Michael Martin, Louisville, KY (US);
Kevin Walsh, Louisville, KY (US);
Julia Aebersold, Floyd Knobs, IN (US);
R. Andrew McGill, Lorton, VA (US);
Stanley V. Stepnowski, Alexandria, VA (US)

(73) Assignees: The United States of America as represented by the Secretary of the Navy, Washington, DC (US); University of Louisville Research Foundation, Inc., Louisville, KY (US)

( * ) Notice: Subject to any disclaimer, the term of this patent is extended or adjusted under 35 U.S.C. 154(b) by 678 days.

(21) Appl. No.: 12/406,756

(22) Filed: Mar. 18, 2009

(65) Prior Publication Data

US 2010/0236341 A1 Sep. 23, 2010

(51) Int. Cl.
*G01N 1/22* (2006.01)

(52) U.S. Cl.
USPC ........................................... 73/863.12

(58) Field of Classification Search
None
See application file for complete search history.

(56) References Cited

U.S. PATENT DOCUMENTS

| | | | |
|---|---|---|---|
| 3,768,300 A | 10/1973 | Nemeth | |
| 4,011,301 A | 3/1977 | Young | |
| 4,698,071 A | 10/1987 | Elias | |
| 4,805,411 A | 2/1989 | Hellat et al. | |
| 4,839,143 A | 6/1989 | Vora et al. | |
| 4,964,309 A | 10/1990 | Jenkins | |
| 5,014,541 A | 5/1991 | Sides et al. | |
| 5,035,776 A | 7/1991 | Knapp et al. | |
| 5,053,343 A | 10/1991 | Vora et al. | |
| 5,083,019 A | 1/1992 | Spangler | |
| 5,092,155 A | 3/1992 | Rounbehler et al. | |
| 5,092,218 A | 3/1992 | Fine et al. | |
| 5,142,143 A | 8/1992 | Fite et al. | |
| 5,395,589 A | 3/1995 | Nacson | |
| 5,437,999 A * | 8/1995 | Diebold et al. | 204/403.11 |
| 5,465,607 A | 11/1995 | Corrigan et al. | |
| 5,578,271 A | 11/1996 | Simon et al. | |
| 5,707,502 A | 1/1998 | McCaffrey et al. | |
| 5,753,832 A | 5/1998 | Bromberg et al. | |

(Continued)

FOREIGN PATENT DOCUMENTS

| | | |
|---|---|---|
| EP | 00649337 B1 | 9/1996 |
| EP | 0502998 B1 | 7/1999 |

(Continued)

OTHER PUBLICATIONS

U.S. Appl. No. 11/881,333, filed Jul. 25, 2007, Martin.

(Continued)

*Primary Examiner* — David Rogers
*Assistant Examiner* — Alex Devito
(74) *Attorney, Agent, or Firm* — Wyatt, Tarrant & Combs, LLP; Stephen C. Hall

(57) ABSTRACT

An analyte collection system device includes an active area that includes a plurality of perforations extending therethrough. The plurality of perforations are arranged to permit passage of an analyte fluid flow through the microscale plate. A heating element is provided for heating the active area, and a thermal distribution layer is disposed over at least a portion of the active area. For cooling the active area at or below an ambient temperature, an active cooler is provided.

23 Claims, 6 Drawing Sheets

U.S. PATENT DOCUMENTS

| | | | |
|---|---|---|---|
| 5,792,423 | A | 8/1998 | Markelov |
| 5,817,012 | A | 10/1998 | Schoendorfer |
| 5,847,291 | A | 12/1998 | Green et al. |
| 5,854,431 | A | 12/1998 | Linker |
| 5,932,482 | A | 8/1999 | Markelov |
| 5,970,803 | A | 10/1999 | Staples et al. |
| 6,001,308 | A | 12/1999 | Marlow et al. |
| 6,020,187 | A * | 2/2000 | Tam .................. 435/287.2 |
| 6,022,748 | A | 2/2000 | Charych et al. |
| 6,057,162 | A | 5/2000 | Rounbehler et al. |
| 6,066,295 | A | 5/2000 | Bernstein et al. |
| 6,085,601 | A | 7/2000 | Linker |
| 6,087,183 | A | 7/2000 | Zaromb |
| 6,171,378 | B1 | 1/2001 | Manginell et al. |
| 6,239,428 | B1 | 5/2001 | Kunz |
| 6,242,195 | B1 | 6/2001 | Idusogie et al. |
| 6,257,835 | B1 | 7/2001 | Kaehler |
| 6,295,860 | B1 | 10/2001 | Sakairi et al. |
| 6,316,268 | B1 | 11/2001 | Yang |
| 6,326,615 | B1 | 12/2001 | Syage et al. |
| 6,345,545 | B1 | 2/2002 | Linker et al. |
| 6,354,160 | B1 | 3/2002 | Staples et al. |
| 6,442,997 | B1 | 9/2002 | Megerle |
| 6,485,987 | B1 | 11/2002 | Charych et al. |
| 6,527,835 | B1 | 3/2003 | Manginell et al. |
| 6,619,143 | B2 | 9/2003 | Danylewych-May et al. |
| 6,666,907 | B1 | 12/2003 | Manginell et al. |
| 6,706,091 | B1 | 3/2004 | Robinson et al. |
| 6,759,013 | B2 * | 7/2004 | Kaltenbach et al. ........ 422/504 |
| 6,811,587 | B1 | 11/2004 | Lorey |
| 6,869,501 | B2 | 3/2005 | Davidson et al. |
| 6,893,879 | B2 | 5/2005 | Petersen et al. |
| 6,914,220 | B2 | 7/2005 | Tian et al. |
| RE38,797 | E | 9/2005 | Linker |
| 6,989,891 | B2 | 1/2006 | Braig |
| 7,104,112 | B2 | 9/2006 | Bonne |
| 7,118,712 | B1 | 10/2006 | Manginell et al. |
| 7,141,786 | B2 | 11/2006 | McGann et al. |
| 7,244,288 | B2 | 7/2007 | Belyakov |
| 7,273,517 | B1 | 9/2007 | Lewis et al. |
| 7,306,649 | B2 | 12/2007 | Boyle |
| 2002/0055184 | A1 | 5/2002 | Naylor et al. |
| 2003/0106799 | A1* | 6/2003 | Covington et al. ........... 204/600 |
| 2004/0035226 | A1 | 2/2004 | Allen et al. |
| 2004/0035227 | A1 | 2/2004 | Allen et al. |
| 2004/0060346 | A1 | 4/2004 | Bonne et al. |
| 2005/0014134 | A1 | 1/2005 | West |
| 2005/0095722 | A1 | 5/2005 | McGill et al. |
| 2005/0226778 | A1 | 10/2005 | Houser et al. |
| 2005/0253061 | A1 | 11/2005 | Cameron et al. |
| 2006/0257287 | A1 | 11/2006 | Call |
| 2007/0084347 | A1 | 4/2007 | Boyle et al. |
| 2007/0176092 | A1 | 8/2007 | Miller et al. |
| 2009/0028208 | A1 | 1/2009 | Martin |
| 2009/0090197 | A1 | 4/2009 | Finlay |

FOREIGN PATENT DOCUMENTS

| | | |
|---|---|---|
| GB | 02243917 A | 11/1991 |
| WO | WO 9735174 A1 | 9/1997 |
| WO | WO 2004052540 A2 | 6/2004 |
| WO | WO 2004083806 A2 | 9/2004 |
| WO | WO 2005029030 A2 | 3/2005 |
| WO | WO 2006013396 A2 | 2/2006 |
| WO | WO 2006046077 A1 | 5/2006 |
| WO | WO 2006046988 A1 | 5/2006 |
| WO | WO 2006073434 A2 | 7/2006 |
| WO | WO 2006073440 A2 | 7/2006 |
| WO | WO 2006104603 A2 | 10/2006 |
| WO | WO 2007041551 A2 | 4/2007 |
| WO | WO 2007044473 A2 | 4/2007 |
| WO | WO 2007056488 A1 | 5/2007 |

OTHER PUBLICATIONS

U.S. Appl. No. 11/542,453, filed Oct. 2, 2006, McGill et al.
U.S. Appl. No. 10/865,685, filed Jun. 10, 2004, McGill et al.
U.S. Appl. No. 12/337,449, filed Dec. 17, 2004, Cambron et al.
Hughes, R.C., et al., "A Mems Based Hybrid Preconcentrator/Chemiresistor Chemical Sensors", Sandia National Laboratories, Albuquerque, N.M., MS 1425, 87185.
McGill, R. A., et al., "Choosing Polymer Coatings for Chemical Sensors", ChemTech, Sep. 1994, pp. 27-37.
Parmeter, J.E., et al., "Overview of Explosives Detection Research and Development in Department 5848 at Sandia National Laboratories", Sandia National Laboratories, Albuquerque, N.M., MS 0782, 87185.
Sandia National Laboratories Fact Sheet, "Micro Analytical Systems Department Technology—μChemLab™".
Berger, T., et al., "Development of Electrochemical Sensors for Trace Detection of Explosives and for the Detection of Chemical Warfare Agents", Proceedings of the SPIE—The International Society for Optical Engineering, vol. 4038, pp. 452-461, 2000.
Cabalo, J., et al., "Trace Detection of Explosives with Low Vapor Emissions by Laser Surface Photofragmentation—Fragment Detection Spectroscopy with an Improved Ionization Probe", Applied Optics, vol. 44, No. 6, pp. 1084-1091, Feb. 20, 2005.
Da Silva, J. A. F., et al., Simulations of silicon microstructure for preconcentration of metallic ions, Microelectronics Technology and Devices. SBMICRO 2003. Proceedings of the Eighteenth International Symposium, Sep. 2003, pp. 420-427, Pennington, NJ, USA.
Davidson, William R., et al., "Vapor and Particle Sampling in the Detection of Terrorists Explosives", Proc. $50^{th}$ ASMS Conf. Mass Spectrom. Allied Top., pp. 697-698, 2002.
Ewing, R. G., et al., "Detection of Volatile Vapours Emitted from Explosives with a Handheld Ion-Mobility Spectrometer", Field Analytical Chemistry and Technology, vol. 5, No. 5, pp. 215-221, 2001.
Fisher, M., et al., "Explosive Detection Using High-Volume Vapor Sampling and Analysis by Trained Canines and Ultra-Trace Detection Equipment", Proceedings of the SPIE—The International Society for Optical Engineering, vol. 5403, No. 1, pp. 409-417, Apr. 12-16, 2004.
Goeringer, Douglas, et al., "Comparison of Atmospheric Pressure Chemical Ionization and Atmospheric Sampling Glow Discharge Ionization Combined with Tandem Mass Spectrometry for Explosives Vapor Detection", Proc. $50^{th}$ ASMS Conf. Mass Spectrom. Allied Top., pp. 707-708, 2002.
Hannum, David W., et al., "Miniaturized Explosive Preconcentrator for Use in a Man-Portable Field Detection System", International Nuclear Materials Management Conference, Phoenix, AZ, Aug. 2, 1999.
Ho, C.K., et al., "Integrated Chemiresistor Sensors with Preconcentrators for Monitoring Volatile Organic Compounds in Water", Proceedings of the 2005 World Water and Environmental Resources Congress. EWRI 2005: Impacts of Global Climate Change, Anchorage, Alaska, May 15, 2005.
Holland, R.M., et al., "Handheld GC instrumentation for Chemical Weapons Convention treaty verification inspections Monograph Title—Field screening methods for hazardous wastes and toxic chemicals. VIP-47, vol. 1", Air and Waste Management Association, Pittsburgh, PA, 1995.
Hughes, David, "Explosive Detection Equipment Firms Develop Enhanced X-Ray and Vapor Technologies", Aviation Week & Space Technology, vol. 134, No. 12, pp. 60-62, Mar. 25, 1991.
Hughes, R. C., et al., "Chemical sensing with an integrated preconcentrator/chemiresistor array", Chemical and Biological Sensors and Analytical Methods II Proceedings of the International Sympoium, 2001, pp. 348-354, Electrochemical Society, Pennington, NJ, USA.
Lucero, Daniel P., "User Requirements and Performance Specifications for Explosive Vapor Detection Systems", Journal of Testing & Evaluation, vol. 13, No. 3, pp. 222-233, 1985.
Martin, Michael, et al., "Microfabricated vapor preconcentrator for portable ion mobility spectroscopy", Sensors and Actuators, B: Chemical, vol. 126, No. 2, Oct. 1, 2007.
McGill, R. A., et al., "A micromachined preconcentrator for enhanced trace detection of illicit materials, 2003 International Semiconductor Device Research Symposium", IEEE, Piscataway, NJ, USA.
Owano, T. G., et al., "Ultrasensitive Detection of Explosives Vapor Using Mid-IR Cavity Ring-Down Spectroscopy", Technical Digest.

Summaries of papers presented at the Conference on Lasers and Electro-Optics, Postconference Technical Digest, pp. 519-520, 2001.

Ritchie, Robert K., et al., "Detection of Explosives, Narcotics, and Taggant Vapors by an Ion Mobility Spectrometry Particle Detector", Proceedings of the SPIE—The International Society for Optical Engineering, vol. 2092, pp. 87-93, 1994.

Parmeter, J.E., et al., "Development of a portable preconcentrator/ion mobility spectrometer system for the trace detection of narcotics", Sandia National Labs. Report, Albuquerque, NM, Aug. 1997.

Parmeter, J.E., et al., "Explosives detection portal for high-volume personnel screening", Proceedings of the 1998 Enforcement and Security Technologies, Boston, MA, 1999.

Parmeter, John, et al., "Overview of Explosives Detection Research and Development in Department 5848 at Sandia National Laboratories", 16$^{th}$ Annual NDIA Security Technology Symposium & Exhibition, Jun. 26-29, 2000.

Rodacy, Philip J., et al., "Unexploded ordnance classification sensor for underwater applications", Sandia National Labs. Report, Albuquerque, NM, Apr. 1, 2000.

Rhykerd, C., et al., "Airport testing an explosives detection portal", Institute of Nuclear Materials Management (INMM) annual meeting, Naples, FL, Jul. 26-30, 1998.

Seman, G., et al., "Detection of Hidden Explosives on Passenger Aircraft Using Hand Searches, Bio-Sensors and Vapour Detectors", Proceedings of the 1977 International Conference on Crime Countermeasures—Science and Engineering, pp. 65-84, 1977.

Sigman, M. E., et al., "Performance Evaluation of an In-Injection Port Thermal Desorption/Gas-Chromatographic/Negative Ion Chemical Ionization Mass Spectrometric Method for Trace Explosive Vapour Analysis", Analytical Chemistry, vol. 73, No. 4, pp. 792-798, Feb. 15, 2001.

Simoes, E.W., et al., "Study of preconcentration of non-polar compounds in microchannels with constrictions", Sensors and Actuators, vol. 115, No. 1, Lausanne, Switzerland, May 23, 2006, pp. 232-239.

Spicer, James B., et al., "Overview: MURI Center on Spectroscopic and Time Domain Detection of Trace Explosives in Condensed and Vapor Phases", Proc. SPIE Int Soc Opt Eng., vol. 5089, No. 2, pp. 1088-1094, 2003.

Staples, Edward J., et al., "Ultrahigh-Speed Chromatography and Virtual Chemical Sensors for Detecting Explosive and Chemical Warfare Agents", IEEE Sensors J., vol. 5, No. 4, pp. 622-631, Aug. 2005.

Voiculescu, I., et al., "Micropreconcentrator for Enhanced Trace Detection of Explosives and Chemical Agents", IEEEE Sensors Journal, vol. 6, No. 5, pp. 1094-1104, Oct. 2006.

"Smiths Detection Introduces Next-Generation Handheld Detector for Narcotics, Explosives, Chemical Warfare Agents and Toxic Industrial Chemicals", Smiths Detection, Pine Brook, NJ, Jun. 3, 2004.

"Technest Provides Status Update on Remote Standoff Chemical Agent and Explosives Detection Sensor Development Program", Technest Holdings Inc., Boston, MA, Jan. 16, 2006.

* cited by examiner

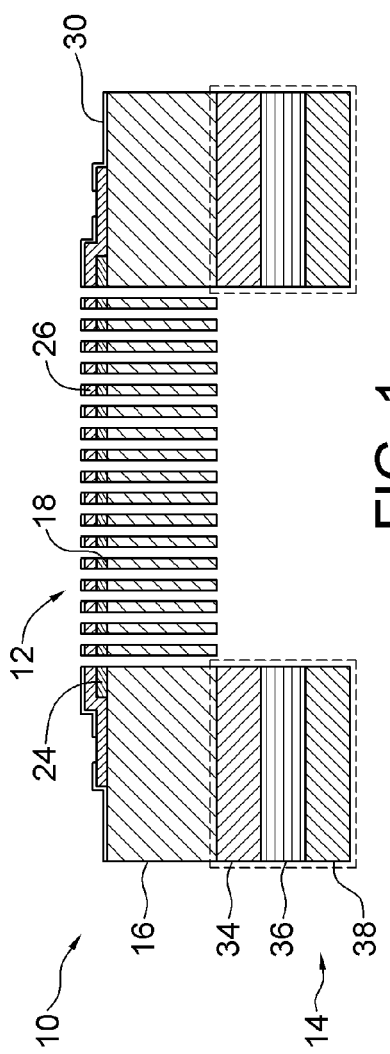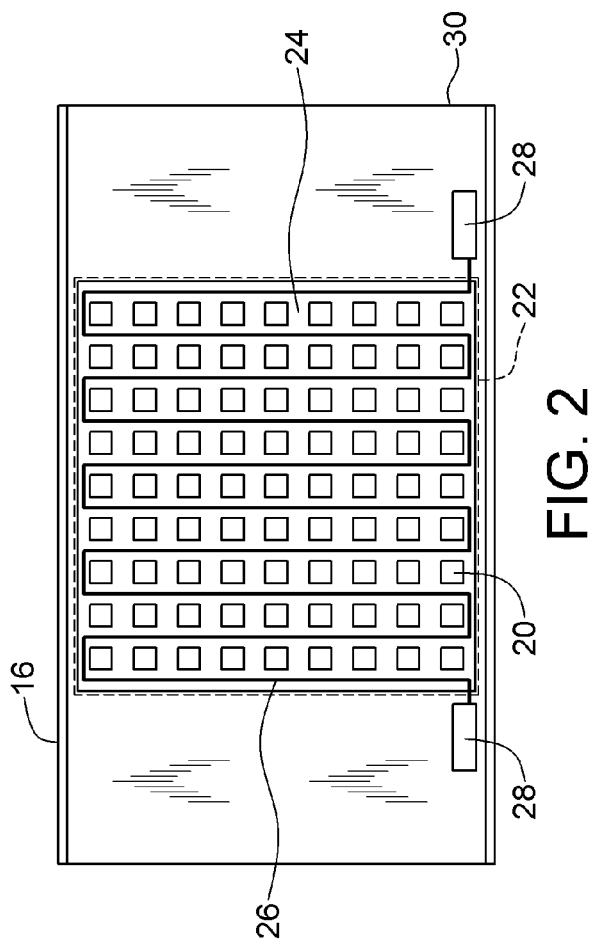

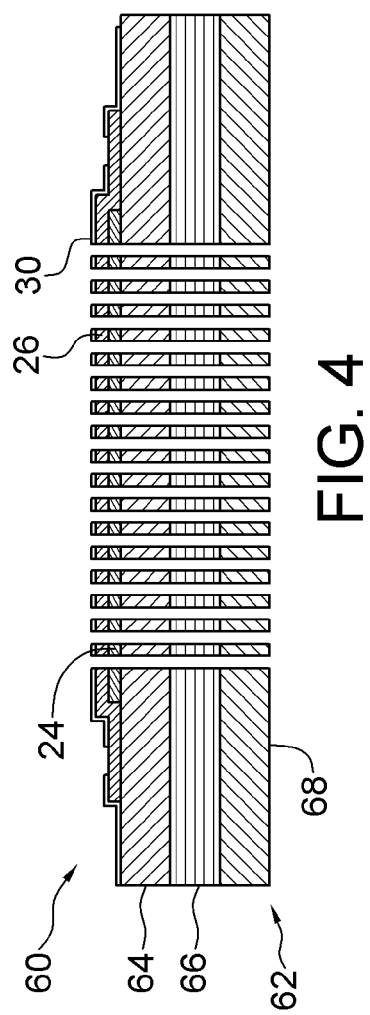
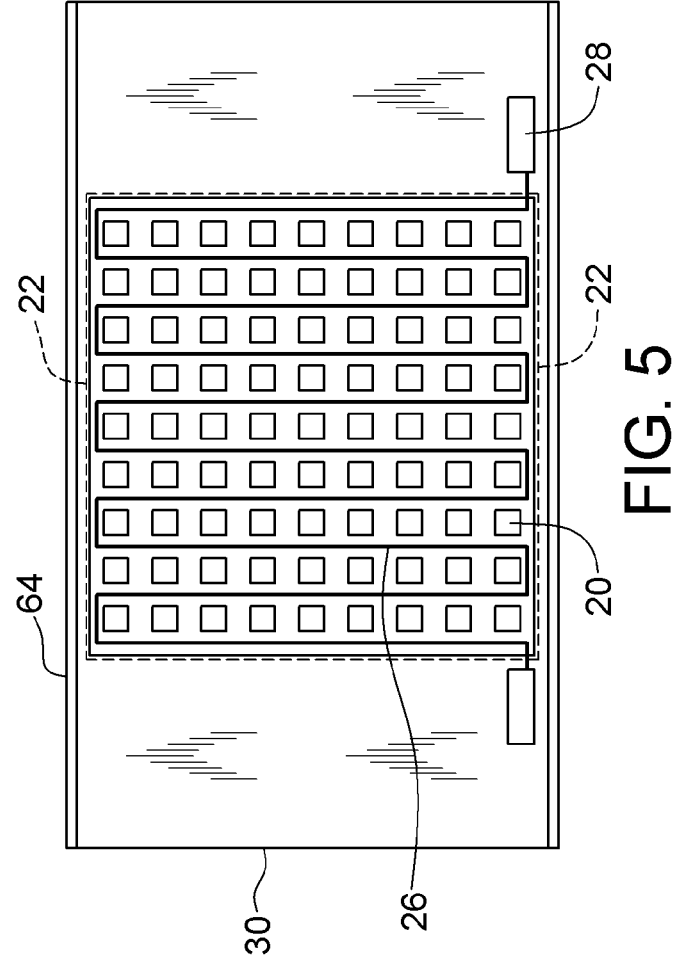

ACTIVELY COOLED VAPOR PRECONCENTRATOR

STATEMENT OF GOVERNMENT INTEREST

This application was made with Government assistance under National Institutes of Hometown Security Grant No. GB051411. The Government has certain rights in this invention.

FIELD OF THE INVENTION

The present invention relates generally to the field of analyte collection. The invention particularly may be useful, for example, in analyte detection and analysis systems and methods, as might be used for the collection, detection, and analysis of a wide range of vapors or gases, particulate, and liquid bound analytes. Another field of the invention is analyte storage and delivery. Embodiments of the invention may be useful, for example, to store and deliver hazardous materials, including explosive related materials, toxic industrial chemicals (TICS), or chemical or biological agents or toxins in a controlled manner.

BACKGROUND OF THE INVENTION

In many analytical systems, discovering the nature of an unknown substance requires the substance to first be collected. There are detector systems that analyze a fluid flow analyte stream, e.g., vapors or gases, particulates, and liquid bound analytes. Some detector systems are based, for example, on an optical analysis that determines analyte characteristics by subjecting a quantity of the analyte to a light beam and measuring the scattering or fluorescence effects. Spectroscopic detector systems, for example, are sometimes based upon the optical effects produced by analyte samples. There are both quantitative and qualitative analysis detector systems.

Before a sample may be analyzed by spectroscopic or many other types of analytical techniques, the sample must be collected and then delivered to a detector system. Many samples of interest are available outside of a controlled setting. One important use for analyte analysis is for safety testing environments that humans occupy. There is a heightened awareness in modern times of the potential for the intentional detonation of explosives or release of chemical or biological agents into environments occupied by humans. For example, environments might include open or enclosed spaces in work environments, public environments, military environments, etc. Many building environments with ducted HVAC (heating ventilation and air conditioning) have the potential for the intentional release of TICS or chemical and biological agents into closed or open spaces occupied by military or civilian personnel. Manufacturing operations also have the potential to permit the escape of hazardous chemicals or biological agents into a manufacturing environment or to an external environment surrounding a manufacturing plant.

In some situations, detection may be desirable in a matter of seconds, but in others, an extended period of time may be used for collection before performing an analysis. An example of the latter case involves workers that may be exposed over a time period to unacceptable levels of harmful agents. Another example of the latter case is when cargo containers are transported from country to country by sea, in which case it may be desirable to collect a sample over a period of several days prior to analysis.

In uncontrolled settings and controlled settings, analytical resolution and the sensitivity of detection are dependent upon the efficiency of analyte collection and the efficacy of delivery of collected analyte to a detection system. It is desirable, for example, to detect very low levels of toxic or hazardous materials in a particular environment. Gas chromatography and other analytical techniques can employ a variety of detector types, and have been demonstrated to be very sensitive analysis methods, among other benefits. Another analytical technique employs a chemresistor based device, which uses a detector whose resistivity changes when it is exposed to particular chemical vapors. Whatever the type of detector system, however, concentrating analyte in a stage prior to the detector system can improve detection limits for the analyte (s) of interest, and can also provide a more reliable quantitative or qualitative determination of an analyte.

Constructing a portable field instrument for collection, storage, concentration, and possibly on-site analysis also presents challenges. Compactness is an important factor to provide an instrument that is useful in the field, but one that competes with other design constraints in the case of a portable field instrument. Among other important factors are the sensitivity discussed above, the time scale required to collect and analyze a sample (preferably short), the amount of fluid flow that may be achieved (limited by tolerable pressure drops and pump capacity) while maintaining good analyte-sorbent material interaction, and the amenability of a device's collection hardware to be integrated with other parts of a field instrument. Low weight, durability, and low electrical power consumption are also desirable qualities for prolonged field use.

It can be difficult to collect a sufficient amount of analyte in particular environmental conditions, such as in ambient surroundings having higher temperatures. For example, if a gas stream is warmer, it may interfere with the efficacy of the analyte collection system. On the other hand, cooling the sorbent material may help to reduce analyte bleed during a collection period. However, providing cooling for a collection device while also allowing for portability, ease of manufacture and use, and relatively low power consumption provides several challenges.

SUMMARY OF THE INVENTION

Embodiments of the present invention provide, among other things, an analyte collection system. An example analyte collection device includes a microscale plate having an active area that includes a plurality of perforations extending therethrough. The plurality of perforations are arranged to permit passage of an analyte fluid flow through the microscale plate. A heating element is provided for heating the active area, and a thermal distribution layer is disposed over at least a portion of the active area. For cooling the active area at or below an ambient temperature, an active cooler is provided.

An analyte collection system having a plurality of preconcentrator chips is also provided according to embodiments of the present invention. According to other embodiments of the invention, a self-contained micro analytical system is provided having a large volume preconcentrator, an analyte collection device, a detector system, a power source, and a controller. Methods for concentrating an analyte from an analyte fluid flow and delivering the analyte are also provided herein.

BRIEF DESCRIPTION OF THE DRAWINGS

FIG. 1 is a side view of an analyte collection device, according to an embodiment of the present invention;

FIG. 2 is a top plan view of the analyte collection device of FIG. 1;

FIG. 4 is a side view of an analyte collection device having an integrated Peltier cooler, according to another embodiment of the present invention;

FIG. 5 is a top plan view of the analyte collection device of FIG. 4;

DETAILED DESCRIPTION

Figure 3:
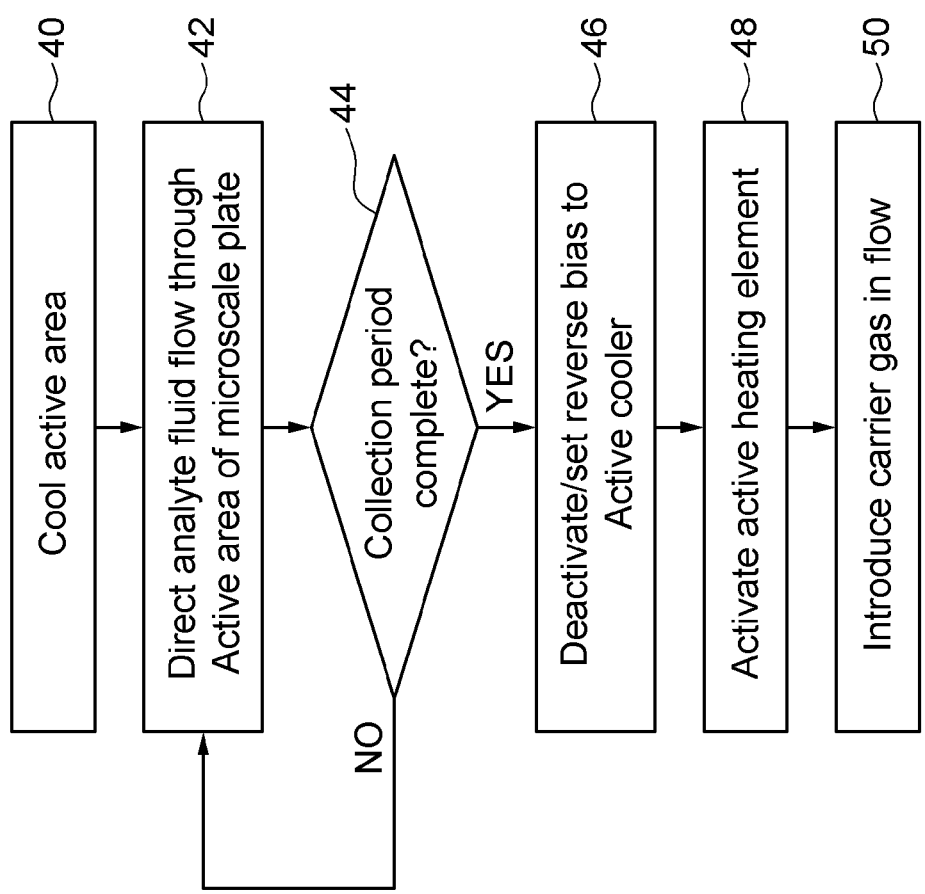
FIG. 3 shows steps in an example preconcentrating method, according to embodiments of the present invention.

Generally, embodiments of the invention provide, among other things, apparatuses and systems for collecting trace vapors from an analyte, such as explosives, chemical agents, and other materials, to concentrate the analyte for subsequent delivery to a detector. Analyte collection systems including a preconcentrator are also provided according to embodiments of the invention.

In exemplary embodiments, an analyte collection device in the form of an actively cooled vapor preconcentrator is provided herein. An example analyte collection device has at least one flow-through microscale plate. This plate, which may be in certain embodiments a sorbent plate, is configured and arranged to collect analyte and deliver a concentrated pulse of analyte, preferably to a detector system, upon demand through heating. The microscale plate includes an active area that has a plurality of perforations (through holes) extending therethrough. During analyte collection, analyte fluid flow, such as analyte vapor, is permitted through the microscale plate. Fluid flow for a collection period is generally perpendicular to the active surface of the microscale plate. Excellent interaction may be achieved between the analyte fluid flow and a sorbent coating on the active surface.

An active heater, such as but not limited to a heating element, is provided to heat the active area quickly during desorption for delivery of the analyte. Preferred embodiment plates include an integrated heater trace (such as a metal resistive trace) as an active heater. Preferably, the active heater is disposed over the surface of the microscale plate and is thermally insulated for allowing quick heating of the active area. For example, the active heater may be disposed on a thermal insulating layer that is formed on the surface of the microscale plate, over the active area.

To improve collection, an active cooler, for example, embodied in a cooling element, is provided for cooling the active area below ambient temperature. The active cooler preferably is in thermal communication with the microscale plate, and more preferably is in thermal communication with a thermal distribution layer disposed over at least a portion of the active area. The thermal distribution layer may be, for example, a layer of weak thermally conductive material. Various embodiments are possible for the active cooler.

The thermal distribution layer, and thus the active area, is cooled by operation of the active cooler during the collection period, whereas the active area is quickly heated via the active heater during adsorption period. Providing a thermally insulated heater with a thermal distribution layer allows the thermal distribution layer to stay cool while collecting analyte from a warmer gas stream. The temperature difference between the collection region (the active surface of the microscale plate) and the impinging gas is a function of the thermal power transferred between them. On the other hand, the ability to generate large amounts of thermal energy via the thermally insulated active heater allows the active area to be rapidly heated to produce a sharp analyte pulse. Thus, after a period of collection, analyte may be provided to a detector system from the microscale plate by heating the plate.

Such analyte collection systems provide preconcentration of vapors while also providing the ability to operate below ambient temperatures or maintain a temperature while collecting in a warmer gas stream. Analyte collection systems according to embodiments of the present invention are particularly useful for use as a second stage preconcentrator, such as in a two-stage, self-contained micro analytical system, though they may also be provided as a stand-alone preconcentrator.

It is possible to use more than one, e.g., a series, of the micro scale plates. In some embodiments, an analyte collection system is provided having a series of preconcentrator chips. Each of the preconcentrator chips includes a microscale plate having an active area with perforations extending therethrough for analyte fluid flow through the plates. The respective active areas of the preconcentrator chips may, though not necessarily, be aligned with one another. Sorbent coating is preferably provided over the active area, along with a heating element and a thermal distribution layer. An active cooler is provided for cooling each of the active areas below an ambient temperature. The active cooler may be, as a non-limiting example, a single element or a plurality of elements. Individual microscale plates may be arranged so that at least some of the respective perforations in the series of plates are at least partially aligned with a solid portion of another plate in the series of plates. In this way, a portion of fluid flow through a hole in one plate is initially brought into contact with a solid portion of a downstream plate before being redirected through a hole of the downstream plate. However, the plates may be arranged in other ways as well.

More than one sorbent may be used on different sections, respectively, of microscale plates, either on a single plate or multiple plates, allowing a device to collect more than one type of analyte. A single plate, for example, may include multiple sorbent sections. In another embodiment, each of a series of plates include a single sorbent while the series of plates includes multiple sorbents by having at least one plate coated with a different sorbent than other plates in the series of plates.

Embodiments of the invention may include both modular collection devices and stand alone analysis devices having a collection device and a detector system, e.g., a transducer, control circuitry, a microprocessor with suitable memory, pneumatic fluidics, and the like. Both modular collection devices and stand alone devices according to embodiments of the invention may be highly compact. An example modular collection device unit can be made small enough, for example, to be conveniently worn on a person, affixed to a vehicle, inserted into the process flow of a machine in a production line, attached to plant life, portions of buildings, in ventilation systems, on cargo, on baggage, in baggage screening areas, etc. For example, a modular collection device of the invention may be clipped to a belt or clothing, or attached to clothing by a hook and loop fastener, e.g., VELCRO®. In an example method of use, such a device may be carried in an environment by a person to collect a sample, and then attached to a detector system after a period of collection. The same is true to a perhaps marginally lesser extent for stand alone analysis devices of the invention, depending upon the scale and type of the detector and detector system used. In an example, a highly compact and complete micro analytical device of the invention includes a detector system in a MEMS integration with a collection device including flow through microscale sorbent plates, a microcontroller, a power source, and electronics.

Preferred embodiments will now be discussed with respect to the drawings. The drawings include schematic figures that may not be to scale, which will be fully understood by skilled artisans with reference to the accompanying description. Dimensions and illustrated devices may be exaggerated for purposes of illustration. Devices and arrays according to embodiments of the invention may be fabricated by processes well-known to the semiconductor device and MEMS communities. From the preferred embodiments, artisans will recognize additional features and broader aspects of the invention.

FIGS. 1-2 show an analyte collection device 10 according to an embodiment of the present invention. The analyte collection device 10 provides, for example, preconcentration of an analyte in a vapor and delivery of the preconcentrated analyte. Generally, the analyte collection device 10 includes a microscale plate 12 and an active cooler 14. The microscale plate 12 provides a hot plate for preconcentration of the analyte. In nonlimiting example embodiments, the microscale plate 12 is within the approximate size range of 1 cm×1 cm, and has a thickness range of 0.5 mm-2 mm with the active area thickness of 3-100 μm.

In preferred embodiments, the microscale plate 12 is microfabricated using known or to-be-known microfabrication techniques. For example, in the embodiment shown in FIGS. 1-2, the microscale plate 12 includes a microfabricated silicon substrate 16 having a generally planar upper surface 18 with a plurality of perforations 20 (through holes) extending therethrough. Preferably, the perforations 20 are arranged in a two-dimensional array, such as the array shown in FIG. 2, though it is to be understood that the particular size, number, and arrangement of the perforations may vary. The planar area over which the perforations 20 are arranged defines an active area 22 (see FIG. 2) on and/or through which analyte is collected. However, it is also contemplated that the active area 22 may extend beyond or be within this planar area, and the active area may also be defined by less than all of the perforations 20. These perforations 20 extend completely through the microscale plate 12 so that in operation, the analyte fluid flow passes through the plurality of perforations as the analyte passes across the active area 22. The plurality of holes may be provided by standard microfabrication techniques, as a nonlimiting example. A particular example microfabrication technique that may be used is reactive ion etching (RIE). In a nonlimiting example embodiment, each of the perforations has an approximate size of 100 μm×300 μm, and depth of 25 μm.

A layer of thermal insulating material 24 is disposed over the surface 18 of the silicon substrate 16 in the active area 22 to provide thermal insulation for an active heater, such as but not limited to an active heating element 26 that heats the active area. The thermal insulating layer 24 is perforated to align with the perforations 20 in the silicon substrate 16. In a nonlimiting example the thermal insulating material is polyimide. Other thermal insulating materials that may be used include parylene, Teflon™ and photoresist. The heating element 26 is disposed over the thermal insulating material 24. An example heating element is a metal resistive trace that is disposed around and between the perforations 20 along the active area 22. Such a resistive trace may be formed on the thermal insulating layer 24, for example, using standard microfabrication techniques. A pair of metal pads 28, as shown in FIG. 2, may be provided as contacts (though other embodiments of contacts are contemplated) for coupling a current to the heating element 26 via a power source and interfacing the heating element with suitable control electronics, such as a controller having suitable logic. In operation, the heating element 26 is activated to release collected analyte after collection. Other heating mechanisms may also be used in embodiments of the invention including, for example, radiation induced heating or heating by conduction or convection mechanisms. However, the heating element 26 embodied in a resistive trace is useful to provide the highly desirable rapid heating and deliver a concentrated pulse. If another heating mechanism is used, it should be chosen and configured to produce a rapid desorption effect, while not interfering with the active cooler 14 used during the collection period.

To assist in cooling the active area 22, a thermal distribution layer 30 is disposed over at least a portion of the active area 22. Preferably, as shown in FIG. 2, the thermal distribution layer 30 is disposed over the silicon substrate 16 and over the entire active area 22, including the thermal insulating layer 24 and the heating element 26. In this way, careful management of thermal energy can be provided to both cool the arriving analyte and heat the active area 22. However, the thermal distribution layer 30 may be configured or disposed in other ways as needed or desired. The thermal distribution layer 30 preferably is a layer of weak thermal conductivity. In other words, it is preferred that the thermal distribution layer be somewhat thermally conductive. An example range of thermal conductivity for the thermal distribution layer 30 is 70 W/m-K-150 W/m-K. In an example embodiment, the thermal distribution layer 30 is a layer of silicon nitride or similarly thermally conductive material. The thermal distribution layer 30 is perforated to align with the perforations in the thermal insulating layer 24 and the silicon substrate 16.

A layer of sorbent material (not shown) preferably is disposed over the layer of partially thermally conductive material 30, over the active area 22. A nonlimiting example for the layer of sorbent material is Naval Research Laboratory's HC polymer. Artisans will find guidance for selecting appropriate sorbent materials, including Naval Research Laboratory's HC polymer, in "Choosing Polymer Coatings for Chemical Sensors", McGill, R. A.; Abraham, M. H.; Grate, J. W., CHEMTECH 24, 9 (1994), p. 27-37. Preferred sorbent coatings will have high temperature stabilities, which are necessary for thermal cycling.

The selectively actuated active cooler 14 is in thermal communication with the thermal distribution layer 30 to cool the active area 22 to at or below ambient temperature at zero analyte flow. An example active cooler 14 is a Peltier cooler that includes three layers. A first electrode/insulator layer 34 is a first electrode and electrical insulator pair that is formed on or attached to the microscale plate 12, and more preferably on the underside of the silicon substrate 16. A p-n semiconductor layer 36 contains p type and n type semiconductor material formed on the first electrode layer 34. Formed on the p-n semiconductor layer 36 is a second electrode and electrical insulator pair layer 38. The first electrode/insulator layer 34 and the second electrode/insulator layer 38 form a reversible cold side and hot side of the peltier junction. Further, as arranged in FIG. 1 and for cooling purposes, the first electrode/insulator layer 34 provides a "cool" plate, while the second electrode/insulator layer 38 provides a "hot" plate. Example materials for the first and/or second electrode/insulator layer 34, 38 and the p-n layer 36 include, but are not limited to, copper on ceramic or an electrically conducting layer on an oxidized silicon wafer, and pellets of n and p type bismuth-telluride electrically connected in series, respectively, with the second electrode/insulator layer 38 identical to the first layer 34. The active cooler 14 is coupled to a suitable controller and power supply (not shown) for selective operation.

In the embodiment shown in FIGS. 1-2, the active cooler 14 is in thermal communication with the silicon substrate 16, which is in turn in thermal communication with the thermal distribution layer 30 disposed over the silicon substrate and extending over the active area 22. Thus, with a Peltier cooler, during analyte collection, to cool the active area 22, the Peltier cooler 14 is activated, and the cooled first electrode layer 34 cools the silicon substrate 16, which in turn cools the thermal distribution layer 30, including over the active area 22.

FIG. 3 shows an example operation of the analyte collection system 10 of FIGS. 1-2. Generally, an example method uses two flows in combination with the active heating and active cooling operations. A collection flow is preferably substantially perpendicular to the active area 22. High flows are possible, as the exit for such substantially perpendicular flows is preferably not into a detector system. The exit collection flow may be released into the environment. In other embodiments, it is collected or stored. In still other embodiments, it is fed back into an input flow stream to capture analyte that may not have been collected in a first pass. The collection flow occurs while the active area 22 is being cooled.

Thus, to concentrate analyte from an analyte fluid flow and deliver the analyte (for example, to a detector), the active area 22 of the microscale plate 12 is cooled (step 40) to at or below ambient temperature at zero analyte flow, such as by activating the active cooler 14. In an example embodiment, selective activation of a Peltier cooler cools the first electrode layer 34, in turn cooling the silicon substrate 16 and thus the thermal distribution layer 30, which is disposed at least partially (and preferably entirely) over the active area 22.

During or after the cooling step 40, the analyte fluid flow is directed (step 42) through the (cooled) active area 22 (that is, in a direction substantially perpendicular to the active surface), via a fan or other suitable apparatus. The weak thermal conductivity of the thermal distribution layer 30, along with high thermal conductivity of the silicon layer 20, helps maintain the active area 22 at or below ambient temperature during this collection period, even if the ambient gas stream is warmer. If the collection period is not yet over (step 44), analyte fluid flow continues to be directed (step 42) through the analyte collection device 10. If the collection period is determined to be over (step 44), the analyte collection device 10 begins adsorption period. Particularly, the active cooler 14 is either turned off or reverse biased (step 46) (that is, operated so that the first electrode 34 is the "hot" electrode and the second electrode is the "cool" electrode). The silicon substrate 16 and thus the thermal distribution layer 30 begin to heat up. Shortly thereafter (e.g., approximately 0-10 seconds), the heating element 26 is activated (step 48) to flash heat the active area 22 and desorb the collected analyte. The active heating element 26 combined with the thermal insulating layer 24 allows the active area 22 to be rapidly heated to produce a sharp analyte pulse. A carrier gas is introduced (step 50) in a flow substantially perpendicular or parallel to the active area 22 to deliver the desorbed analyte. The carrier gas, such as but not limited to air or nitrogen, delivers the collected analyte to another device. A pump, for example, may be employed to deliver the carrier gas. An example destination device is a detector, such as the example detector shown in FIG. 7.

Because certain Peltier solid state coolers can be relatively inefficient, careful management of the cooler size, and thus power consumption should be considered to improve cooler efficiency, particularly if the preconcentrator is used in portable applications. For example, the thermal mass of all components should be minimized and well insulated.

In an alternative embodiment analyte collection device, the active area 22 is cooled using the adiabatic expansion of gasses, i.e., the Joule-Thomson effect. Thus, in an example analyte collection device according to this embodiment, the Peltier cooling system 14 is replaced with a gas delivery system (not shown) including outer, thermally conductive plates in contact with the silicon substrate 16. By adiabatic expansion of the gasses within the gas delivery system, the thermally conductive plates are cooled, thus cooling the silicon substrate 16 and in turn cooling the thermal distribution layer 30 and the active area 22. Except for the substitution of the gas delivery system for the Peltier cooling system 14, this alternative embodiment may be made similarly to the analyte collection device 10 shown in FIGS. 1-2.

Similar to the gas delivery system described above, another alternative embodiment analyte collection device replaces the Peltier cooling system 14 with a chilled liquid delivery system. For example, a chilled liquid delivery system (not shown) includes outer, thermally conductive plates, which are disposed in contact with silicon substrate 16. By delivery of the chilled liquid through the system, the thermally conductive plates are cooled, thus cooling the silicon substrate 16 and in turn cooling the thermal distribution layer 30 and the active area 22. Except for the substitution of the chilled liquid delivery system for the Peltier cooling system 14, this alternative embodiment may be made similarly to the analyte collection device shown in FIGS. 1-2.

Other nonlimiting example active coolers include direct vapor compression (vapor-compression cycle cooling), thermionic, vortex tubes, air cycle, magnetic cooling, Stirling cycle, Malone refrigeration, thermoacoustics, pulse tube, water cycle systems, etc. The present invention is not intended to be limited to a specific type of active cooler.

Though the silicon substrate 16 is preferred for providing support to the microscale plate 12, it is not required in all embodiments. The material for the plates may be any material amenable to microfabrication processing. This includes semiconductors and dielectrics. Silicon semiconductors are suitable, as are Group III-V materials. Dielectrics include ceramics, glass, polymers, crystalline quartz, fused silica, etc. To the extent the substrate is used for heat transfer from the cooling element, it is desired that the substrate exhibit thermal conductive properties. However, it is also contemplated that the active cooler cool the active area 22 directly via the thermal distribution layer 30.

In another alternative analyte collection device 60, shown in FIGS. 4-5, the microscale plate itself is fabricated as a Peltier cooler (or part of a Peltier cooler) to provide the active cooler. Thus, instead of the silicon substrate 16 for structural support as in the analyte collection system shown in FIG. 1-2, an actively cooling substrate 62 is provided from a stack of materials to provide a first electrode/insulator layer 64, a p-n layer 66, and a second electrode/insulator layer 68.

Examples for the layers 64, 66, 68 include, but are not limited to, an oxidized silicon wafer with conductive traces, pellets of p and n type bismuth telluride or silicon, and a second oxidized silicon wafer with conductive traces. Such layers may be formed, for example, using known or to-beknown microfabrication techniques. The layers 64 or 68 of the cooling substrate 62 may be coupled to a suitable controller and power supply for operation.

The actively cooling substrate 62 is perforated, such as by standard microfabrication techniques, to provide the perforations 20 and define the active area 22. In the embodiment shown in FIG. 4, the first electrode/insulator layer 64 provides the "cool" electrode, and the active area 22 is defined at or near the perforated portion of the first electrode layer 64 (as shown in FIG. 5). Thus, as with the embodiment shown in FIGS. 1-2, the active area 22 is preferably covered with the thermal insulation layer 24, the heating element 26 (with pads 28), and the thermal distribution layer 30. The active area 22 is cooled by the perforated thermoelectric junction provided by the actively cooling substrate 62.

The silicon substrate 16 of FIGS. 1-2 is helpful in particular embodiments to provide structural support to the microscale plate, and more particularly the active area 22. However, it is also contemplated that the active surface of the microscale plate may include a three (or more) layer stack without silicon behind it. For example, the silicon substrate 16 may be replaced with a silicon outer frame (not shown) that supports at a perimeter, but is not directly behind, the active surface. The active surface in an example embodiment may be formed by the thermal insulating layer (e.g., polyimide) with the heating element formed thereon, and the thermal distribution layer (e.g., silicon nitride) formed as an upper layer. The thermal distribution layer may be embodied in a plate that extends to the silicon frame for outer support and for cooling. Particularly, an active cooler, including but not limited to a Peltier cooler, a chilled liquid delivery system, and/or a gas delivery system with a device for expanding the gas, can be in thermal communication with the silicon frame to cool the frame and in turn cool the thermal distribution layer.

Another alternative embodiment analyte collection device has an active area that includes only two materials instead of the several materials shown in the analyte collection device 10 of FIGS. 1-2. This alternative embodiment includes a thermal distribution layer of a weak thermally conductive material and a heating element disposed thereon. The thermal distribution layer is formed over the silicon substrate 16 or suspended over a silicon frame. The thermal insulating layer is omitted from this example embodiment.

Though the heating element 26 shown in FIGS. 1-2 and 4-5 is in a particular arrangement to surround the perforations 20, alternative arrangements for the heating element(s) are possible. For example, in an alternative analyte collection device, a second set of heaters are placed near the edge of the perforations 30 in the active area 22. The heaters are heated during collection to prevent analyte from accumulating on cool silicon surfaces not already covered. It is also contemplated that the resistive traces of the example heating element 26 may be used to divide the active area 22 into a plurality of zones for collection and delivery.

Figure 6:
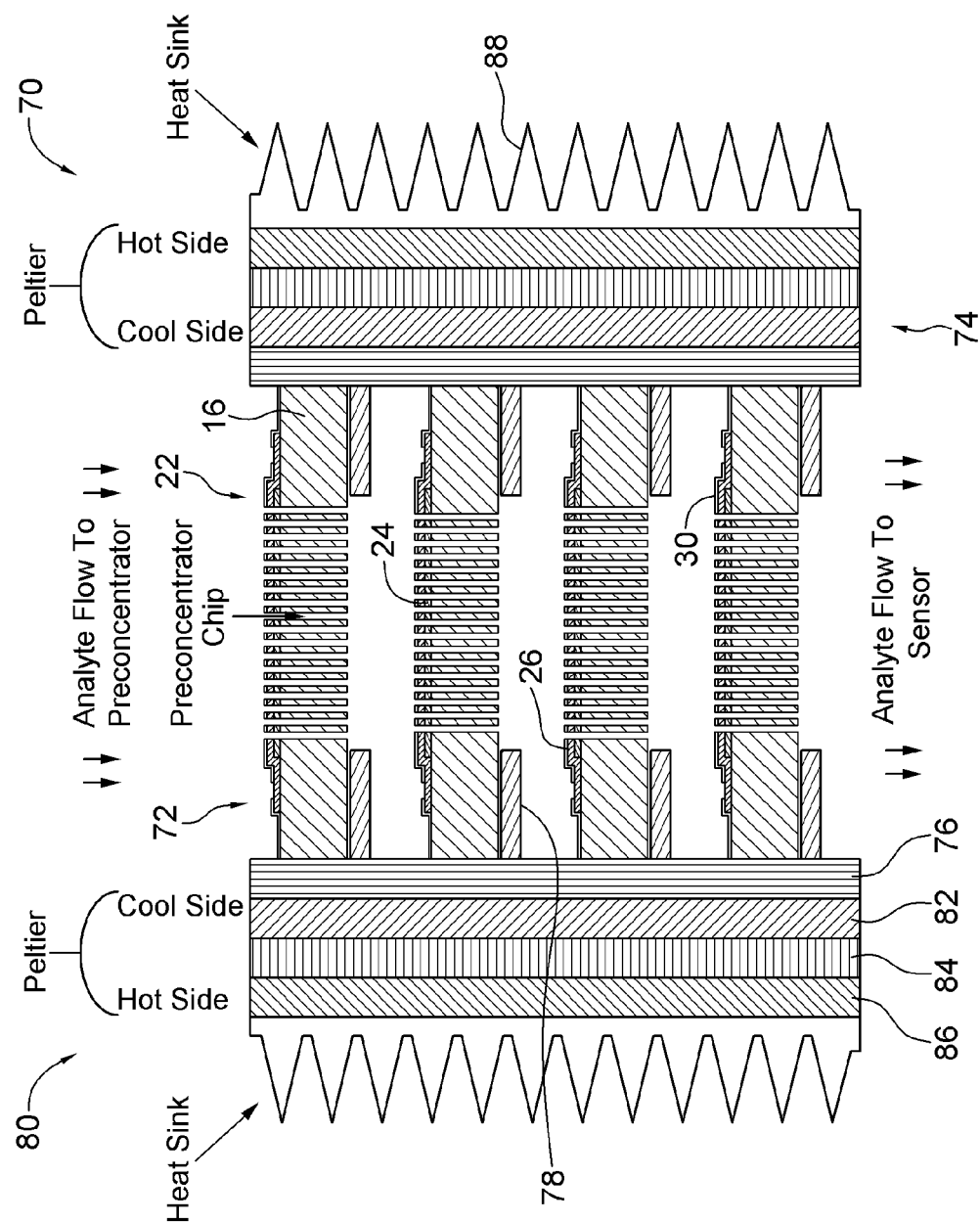
FIG. 6 is a side view of an analyte collection system having a plurality of flow-through preconcentrator chips, according to another embodiment of the present invention.

In another alternative analyte collection system 70 of the present invention, shown in FIG. 6, a plurality of preconcentrator chips 72 are provided in a stacked arrangement. Each of the preconcentrator chips 72 includes the microscale plate 12 shown in FIGS. 1-2. Particularly, each of the preconcentrator chips 72 includes, in order, the silicon substrate 16, having perforations 20 to provide an active area 22 thereon, the thermal insulating layer 24, the metal heating element 26, and the thermal distribution layer 30.

To support the preconcentrator chips 72 and providing cooling to the thermal distribution layers 30, a set of vertically stacked (in the orientation shown in FIG. 6) thermally conductive chip mounts 74 are provided, including an inner, vertical, thermally conductive surface 76 and a plurality of inwardly extending supports 78 for holding individual chips. Nonlimiting example materials for the thermally conductive surface 76 and the inwardly extending supports 78 include aluminum and silver, respectively. A vertically extending Peltier cooler 80 surrounds the thermally conductive chip mounts 74, and includes a first, inner electrode/insulator pair 82 (a "cool" side), a p-n layer 84, and a second, outer electrode/insulator pair 86 (a "hot" side). For distributing heat from the second, "hot" electrode 86, a heat sink 88 may be provided on an outer portion of the analyte collection system 70. The heat sink 88 may include, for example, a machined aluminum block.

Operation of the analyte collection system 70 is similar to that of the system 10 shown in FIGS. 1-2. The vertical arrangement of the Peltier cooler 80 allows cooling of the active areas of each of the preconcentrator chips 72. Analyte flow to the preconcentrator chips 72 preferably runs from top to bottom, perpendicular to the active areas 22 and through the perforations 20 in each chip. However, after desorption, the analyte preferably also flows perpendicular to the active areas 22 towards a sensor, in contrast to the embodiment shown in FIGS. 1-2 (which preferably, though not necessarily, uses desorption flow in a direction parallel to the active area).

Figure 7:
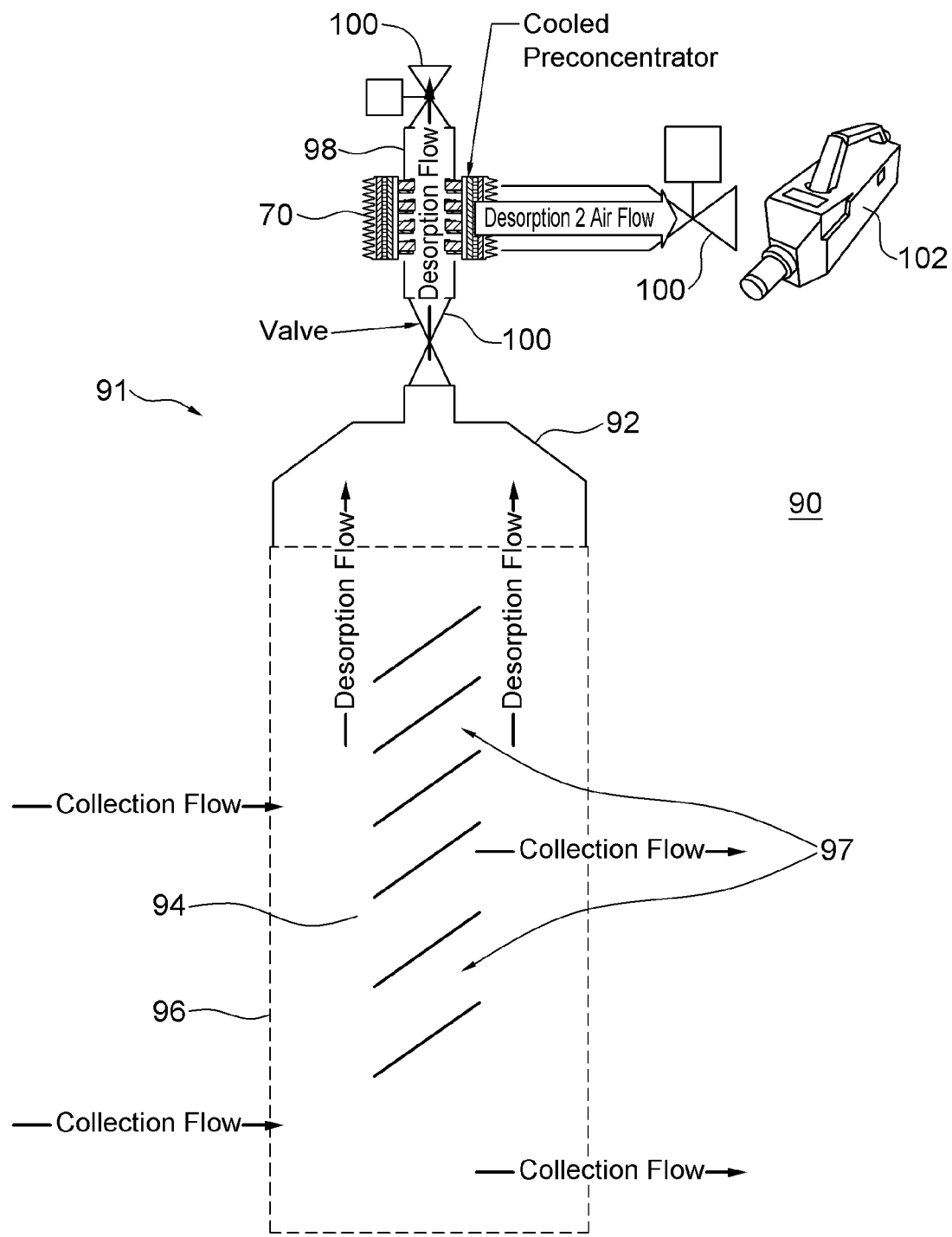
FIG. 7 shows fluid flow in a self contained micro analytical system including an analyte collection system according to an embodiment of the present invention.
Figure 8:
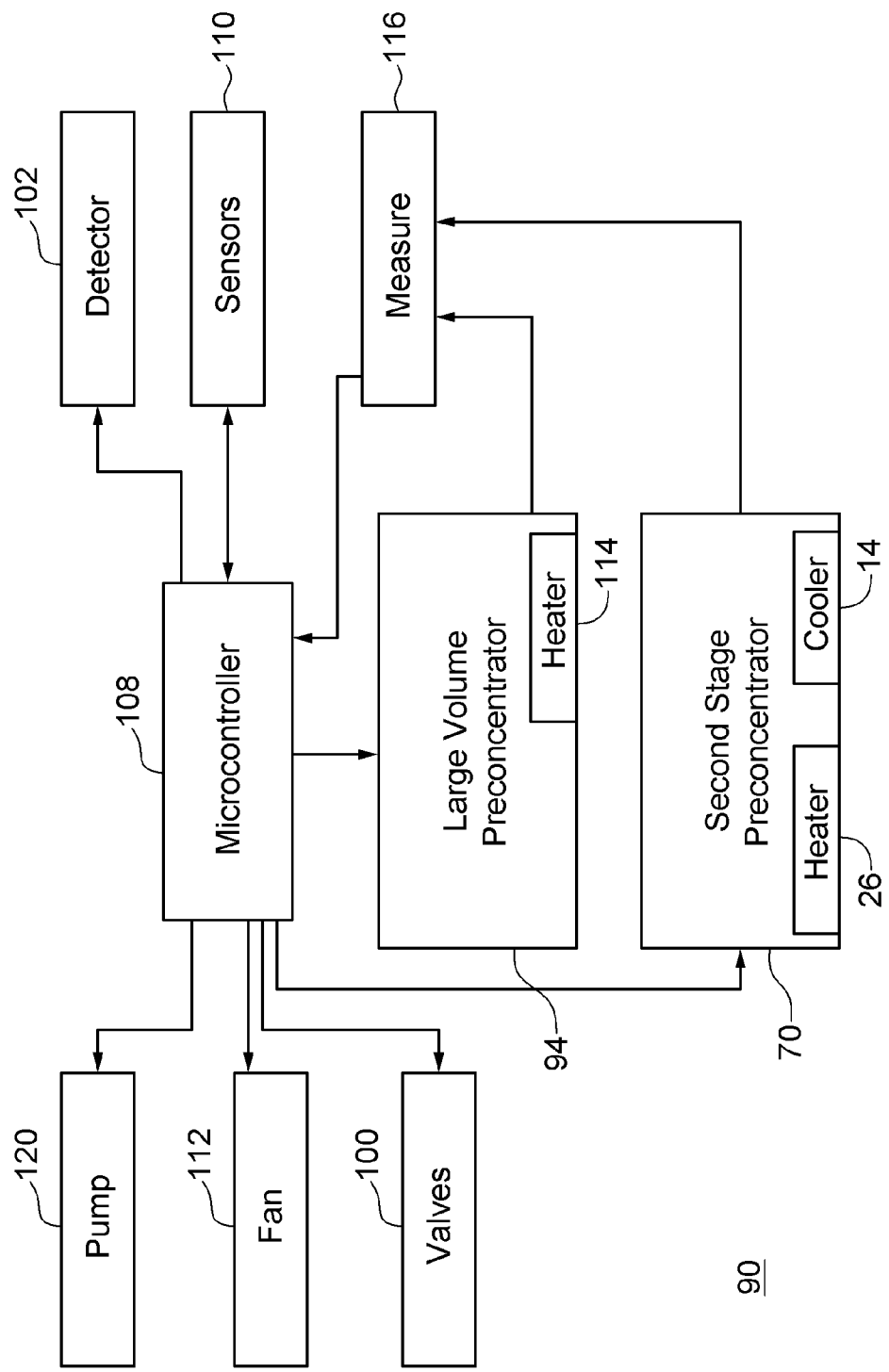
FIG. 8 shows components of the micro analytical system of FIG. 7.

The analyte collection device 10, 60, 70 may be used as part of a micro analytical system. Preferably, the micro analytical system is self-contained, though this is not necessary in all embodiments. An example of a micro analytical system 90, shown in FIG. 7, incorporating the analyte collection device 70 includes a two-stage vapor preconcentrator 91 contained within a housing 92. The housing 92 may be configured to be highly compact for a self-contained field analysis device, for example. The two-stage preconcentrator 91 includes a large volume preconcentrator 94 in a first chamber 96, which preferably includes one or more perforated, sorbent plates 97 for collecting analyte. A collection flow, as shown in FIG. 7, preferably runs through the large volume preconcentrator 94, for example perpendicular to surfaces of the sorbent plates 97. After a certain collection period, desorbed analyte is carried via a carrier gas in a desorption flow to a second chamber 98, which houses the analyte collection device 70 or analyte collection device of other embodiments of the present invention. The walls of the housing 92, including those of the first chamber 96 and the second chamber 98, should be inert to the analyte(s) of interest, either because of material properties or by active heating to the active areas to avoid sorption. A valve 100 may be disposed between the first and second chambers 96, 98 (that is, between the large volume preconcentrator 94 and the actively cooled analyte collection device 70) for selectively allowing fluid flow to the second chamber 98. In certain embodiments, the large volume preconcentrator 94 may have a narrowed end to interface with the second chamber 98. After a collection period by the analyte collection device 70, during which air flow preferably is in a direction perpendicular to the active area(s) 22 of the analyte collection device, the desorption flow runs parallel to the active area(s) for output to a detector system 102, for example via a valve 100. An example detector system 102 may include but is not limited to an ion mobility spectrometer. Fluid flow may be controlled by a pump that may or may not be integral to the detector and valves 100 under suitable integrated electronics. FIG. 8 is a block diagram of the micro analytical system 90 of FIG. 7. The large volume preconcentrator 94, the second stage (cooled) preconcentrator 70, and the detector 102 are powered by a suitable power supply (not shown), e.g., a battery, and controlled by a controller, such as but not limited to a microcontroller 108 having suitable logic. The microcontroller 108, which is provided with feedback via one or more sensors 110, selectively controls operation of an airflow system including one or more fans or pumps 112 and the valves 100, and further selectively controls the large volume preconcentrator 94 and second stage preconcentrator 70. The valves operate to permit flows to be directed into and out of the large volume preconcentrator 94 and the second stage preconcentrator 70 during periods of analyte collection and concentration therein.

Generally, the microcontroller 108 runs the overall system 90. For example, the microcontroller 108 directs the fans 112 and valves 100 for inducing collection flows, and one or more pumps 120 for inducing desorption flows. In operating the large volume preconcentrator 94, the microcontroller 108 opens an outlet and provides power to the fan 112 to induce a flow through the plate or plates. After a collection period, the microcontroller 108 selectively operates a heater 114 during desorption. If multiple heaters (e.g., traces) are used, the microcontroller 108 preferably controls each heater individually. For example, if multiple zones are used, the individual heaters in these zones may be operated at different times to enhance selectivity of the system. The microcontroller 108 may embody or access memory for sensor 110 data and analysis. Similarly, during the second preconcentration stage, the microcontroller 108 selectively operates the active cooler(s) 14 during the collection period, and the active heating element(s) 26 during the desorption period.

During collection, the large volume preconcentrator is unenergized and left at ambient temperature. Once the collection period has ended, a valve downstream of the large volume preconcentrator (not shown) is closed and the valve(s) 100 between the preconcentrators and downstream of the actively cooled device is/are opened. Simultaneously, the actively cooled analyte collection device 70 is cooled followed by the thermal desorption of the large volume preconcentrator 94, effectively transferring collected analyte to the actively cooled preconcentrator. The valve(s) 100 between large volume and actively cooled preconcentrators is/are closed. With flow established to the detector 102, cooling is turned off and the active area of the cooled preconcentrator 70 is heated. Suitable measurements 116 from the large volume preconcentrator 94 and the second stage preconcentrator 70 may be provided.

Various devices and methods for analyte collection have been shown and described, having various features and benefits. Example actively cooled vapor preconcentrators can operate at or below ambient temperatures or maintain a temperature while collecting in a warmer gas stream. By providing a thermally insulated heater with a weak thermal conductor, the nitride can stay cool while collecting analyte from a warmer gas stream. The temperature difference between a collection region and impinging gas is a function of the thermal power transferred between them. The ability to generate large amounts of thermal energy via the microfabricated heater traces combined with the thermally insulating polyimide allows the active surface to be rapidly heated to produce a sharp analyte pulse.

Analyte collection devices according to embodiments of the present invention can be used as second stage preconcentrators. Actively cooled vapor preconcentrators can enhance the detection limits of various trace detectors for explosives, chemical agents, toxic industrial chemicals, and other illicit materials in portable and stationary applications. Example preconcentrators can enhance detection limits for detectors and analytes in liquid environments. Alternative or additional applications include, but are not limited to, trace detection of biological molecules. Actively cooled vapor preconcentrators according to particular embodiments may be applied for calibrated vapor delivery.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An analyte collection device, the device comprising:
   a microscale plate having an upper surface and an active area, the active area including a plurality of perforations extending therethrough, the plurality of perforations being arranged to permit passage of an analyte fluid flow through said microscale plate;
   a heating element for heating said active area;
   a thermal distribution layer disposed over at least a portion of the active area;
   a thermal insulating layer disposed on the upper surface; and
   an active cooler for cooling the active area at or below an ambient temperature,
   wherein said thermal distribution layer comprises a layer of weak thermally conductive material disposed over the thermal insulating layer for conducting thermal energy away from the microscale plate,
   and wherein the thermal insulating layer is positioned between the upper surface of the microscale plate and the thermal distribution layer.

2. The analyte collection device of claim 1, wherein said heating element comprises a resistive trace formed on the active area.

3. The analyte collection device of claim 1, wherein said microscale plate comprises: a silicon substrate having an upper surface; wherein said heating element is formed on said thermal insulating layer.

4. The analyte collection device of claim 1, wherein said thermally conductive material comprises silicon nitride.

5. The analyte collection device of claim 1, wherein said active cooler comprises a Peltier cooler in thermal communication with said thermal distribution layer.

6. The analyte collection device of claim 1, further comprising:
   a layer of sorbent material disposed over said thermal distribution layer.

7. The analyte collection device of claim 5, wherein the Peltier cooler comprises a first electrode/dielectric pair formed on the microscale plate, a P—N layer formed on the first electrode/dielectric layer, and a second electrode/dielectric layer formed on the P—N layer.

8. The analyte collection device of claim 1, wherein said microscale plate comprises:
   a first electrode/dielectric layer;
   a P—N layer formed on said first electrode/dielectric layer; and
   a second electrode/dielectric layer formed on said P—N layer;
   said first electrode/dielectric layer and said second electrode/dielectric layer providing a electrical series connection between P and N type conductors.

9. The analyte collection device of claim 1, wherein said active cooler comprises a chilled liquid delivery system in communication with said microscale plate.

10. The analyte collection device of claim 1, wherein said active cooler comprises:
   a gas delivery system in communication with said microscale plate;
   a device for expanding a gas for delivering via said gas delivery system.

11. The analyte collection device of claim 1, further comprising:
   a silicon frame connected to and supporting said microscale plate;
   wherein said thermal distribution layer connects said microscale plate and said silicon frame;
   wherein said active cooler is positioned to cool said thermal distribution layer.

12. An analyte collection system, comprising:
   a plurality of preconcentrator chips, each of said preconcentrator chips comprising:
   a microscale plate having an active area, the active area including a plurality of perforations extending therethrough, the plurality of perforations being arranged to permit passage of an analyte fluid flow through said microscale plate;
   a heating element for heating said active area;
   a thermal distribution layer disposed over at least a portion of the active area;
   an active cooler for cooling each of the active areas below an ambient temperature; and
   a thermally conductive chip support for conducting thermal energy away from said preconcentrator chips thereby cooling said preconcentrator chips, said thermally conductive chip support being configured to mount each of said plurality of preconcentrator chips,
   wherein said thermal distribution layer is disposed over a thermal insulating layer, and the thermal insulating layer is positioned between the microscale plate and the thermal distribution layer.

13. The analyte collection system of claim 12, wherein said active cooler comprises a Peltier cooler in thermal communication with said thermally conductive chip support, said Peltier cooler comprising a first electrode/dielectric layer and a second electrode/dielectric layer providing a electrical series connection between P and N type conductors.

14. The analyte collection system of claim 13, further comprising:
   a heat sink in thermal communication with said second electrode.

15. A micro analytical system, the system comprising:
   a large volume preconcentrator;
   an analyte collection device according to claim 1, said analyte collection device being in fluid communication with said large volume preconcentrator;
   a detector system;
   a power source; and
   a controller.

16. The system of claim 15, further comprising:
   a housing for said analyte collection device and said large volume preconcentrator;
   an inlet to said housing;
   an outlet to said housing; and
   means for inducing analyte fluid flow.

17. The system of claim 16, wherein said means for inducing flow comprises a low power fan.

18. The system of claim 16, wherein said large volume preconcentrator and said analyte collection device are separated by a valve.

19. A method for concentrating analyte from an analyte fluid flow and delivering the analyte, the method comprising:
   cooling an active area of a microscale plate to a temperature at or below an ambient temperature, the active area including a plurality of perforations extending therethrough to permit passage of an analyte fluid flow through said microscale plate;
   directing analyte fluid flow substantially perpendicular to the active area and through the plurality of perforations to concentrate analyte on a sorbent disposed on the active area;
   heating the active area to desorb the analyte;
   delivering the desorbed analyte in a flow substantially parallel to the active area,
   wherein said cooling the active area comprises cooling a thermal distribution layer for conducting thermal energy away from the microscale plate, the thermal distribution layer being disposed over at least a portion of the active area and over a thermal insulating layer, and the thermal insulating layer being positioned between the microscale plate and the thermal distribution layer.

20. The method of claim 19, wherein said cooling the active area comprises at least one of activating a Peltier cooler, delivering a chilled liquid, vapor-compression cycle cooling, thermionic cooling, vortex tube cooling, air cycle cooling, magnetic cooling, Stirling cycle cooling, Malone refrigeration acoustic cooling, pulse tube cooling, water cycle system cooling, and delivering an adiabatically expanded gas.

21. The method of claim 19, wherein said heating the active area comprises activating an active heater to flash heat the active area.

22. The method of claim 21, wherein said cooling the active area comprises activating a Peltier cooler, and wherein said heating the active area further comprises reversing operation of the Peltier cooler.

23. The method of claim 19, wherein said heating the active area desorbs the analyte in a direction perpendicular to the active area.

* * * * *